(12) United States Patent
Kang et al.

(10) Patent No.: US 9,125,594 B2
(45) Date of Patent: Sep. 8, 2015

(54) METHOD AND SYSTEM FOR CONTOUR FITTING AND POSTURE IDENTIFICATION, AND METHOD FOR CONTOUR MODEL ADAPTATION

(75) Inventors: Chia Hao Kang, Tainan (TW); Yu Hsien Chiu, Kaohsiung County (TW); Tsung Ming Hsieh, Tainan (TW); Chi Chun Hsia, Kaohsiung (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 0 days.

(21) Appl. No.: 12/332,085

(22) Filed: Dec. 10, 2008

(65) Prior Publication Data

US 2010/0069795 A1    Mar. 18, 2010

(30) Foreign Application Priority Data

Sep. 17, 2008  (TW) .............................. 97135567 A (51) Int. Cl.
| | |
|---|---|
| *A61B 5/103* | (2006.01) |
| *A61B 5/00* | (2006.01) |
| *A61B 5/11* | (2006.01) |
| *A61B 5/107* | (2006.01) |

(52) U.S. Cl.
CPC ............... *A61B 5/103* (2013.01); *A61B 5/1036* (2013.01); *A61B 5/1116* (2013.01); *A61B 5/447* (2013.01); *A61B 5/7246* (2013.01); *A61B 5/7264* (2013.01); *A61B 5/7267* (2013.01); *A61B 5/1077* (2013.01); *A61B 5/4561* (2013.01)

(58) Field of Classification Search
CPC .... A61B 5/103; A61B 5/1036; A61B 5/1077; A61B 5/1116; A61B 5/447; A61B 5/4561; A61B 5/7246; A61B 5/7264; A61B 5/7267
USPC ......................................................... 600/595
See application file for complete search history.

(56) References Cited

U.S. PATENT DOCUMENTS

| | | | |
|---|---|---|---|
| 5,038,137 A | 8/1991 | Lloyd | |
| 5,184,112 A | 2/1993 | Gusakov | |
| 5,884,488 A | 3/1999 | Gram | |
| 5,914,660 A | 6/1999 | Mesibov | |
| 6,468,234 B1 | 10/2002 | Van Der Loos | |
| 6,791,460 B2 | 9/2004 | Dixon | |

(Continued)

OTHER PUBLICATIONS

Seo et al., Bed-type Robotic System for the Bedridden, Jul. 2005, Proceedings of the 2005 IEEE/ASME International Conference on Advanced Intelligent Mechatronics, pp. 1170-1175.*

(Continued)

*Primary Examiner* — Lee S Cohen
*Assistant Examiner* — Emily Lloyd
(74) *Attorney, Agent, or Firm* — WPAT, P.C.; Anthony King; Kay Yang (57) ABSTRACT

A method for contour fitting and posture identification initially receives sensor data formed of a plurality of sensor signals. Thereafter at least one candidate posture or contour is determined from a set of at least one posture model based on the sensor data. Finally, user posture is determined from the at least one candidate posture through a decision making process. The sensor data can also be used to modify the at least one posture model for increasing identification accuracy. The sampling frequency of each sensor signal is dynamically adjusted to receive the sensor data in a nearly real-time manner.

21 Claims, 8 Drawing Sheets

(56) References Cited

U.S. PATENT DOCUMENTS

| | | |
|---|---|---|
| 2003/0055321 A1 | 3/2003 | Watrous et al. |
| 2005/0172311 A1* | 8/2005 | Hjelt et al. ............... 725/12 |
| 2007/0113629 A1 | 5/2007 | Lohmiller et al. |

OTHER PUBLICATIONS

Nishida et al, "Monitoring patient respiration and posture using human symbiosis system", Intelligent Robots and Systems, Proceedings of the 1997 IEEE/RSJ International Conference on IROS '97, vol. 2, pp. 632-639, 1997.

Harada, et.al, "Body parts positions and posture estimation system based on pressure distribution image", IEEE Proc. of International Conference on Robotics and Automation, vol. 2, pp. 968-975, 1999.

Harada, et.al, "Infant Behavior Recognition System Based on Pressure Distribution Image", Proceeding of the 2000 IEEE International Conference on Robotics and Automation, San Francisco, pp. 4082-4088, 2000.

Harada, "Estimation of Bed-Ridden Human's Gross and Slight Movement Based on Pressure Sensors Distribution Bed", ICRA 2002: 3795-3800.

Chi-Chun Hsia et.al, "Bayesian Classification for Bed Posture Detection Based on Kurtosis and Skewness Estimation", IEEE Int'l Conference on e-Health Networking, Applications and Service (Healthcom), 2008, pp. 188-191.

IEEE Healthcom 2008, 2008 10th IEEE International Conference on e-Health Networking, Applications and Services, Jul. 7-9, 2008, Biopolis, Singapore, List of Paper Session 7 Sensors and Bio Signal Processing Papers, 2 pages.

Japanese Office Action dated Apr. 5, 2011 for 2008-291937, which is a corresponding Japanese application.

Yoshifumi Nishida et al., Unrestrained and Non-invasive Monitoring of Human's Respiration and Posture in Sleep Using Pressure Sensors, Proceedings of the Robotic Society of Japan, Jul. 1998, pp. 705-711, vol. 16, No. 5, only "3.2 Posture Recognition Algorithm" considered as this was the only translated portion provided of Cite 2.

Yoshifumi Nishida et al., Monitoring Patient Respiration and Posture Using Human Symbiosis System, Proceedings of the 1997 IEEE/RSJ International Conference on Intelligent Robots and Systems, Sep. 1997, pp. 632-639, vol. 2.

* cited by examiner

METHOD AND SYSTEM FOR CONTOUR FITTING AND POSTURE IDENTIFICATION, AND METHOD FOR CONTOUR MODEL ADAPTATION

BACKGROUND OF THE INVENTION

1. Field of the Invention

The present invention relates to a method and system for contour fitting and posture identification that is on a nearly real-time basis.

2. Description of the Related Art

Due to the growth of the elderly population, the demand for elderly health-care and daily nursing care services will increase in the near future. However, the manpower growth in these services cannot keep pace with the elderly population growth. Thus, the human resources for health and nursing care will be very limited, and heavily disabled people, who require intensive care, will suffer the most under the scarce labor situation. Without enough medical resources, some nursing care issues such as pressure ulcer prevention management will become critical to the heavily disabled people. Therefore, developing an auxiliary system that can be used in medical facilities, for example the pressure ulcer prevention management, for the heavily disabled people becomes a very important research direction.

Pressure ulcers result from tissue death due to lack of oxygen supply. While remaining in the same posture for a long time, localized skin and tissue death may occur due to prolonged, irreversible ischemia brought by compression of soft tissue. In order to reduce the risk of pressure ulcer development, a medical attendant has to regularly change the position of a heavily disabled patient in bed for releasing compressed tissue from pressure.

In order to prevent patients from remaining in the same posture for an extended time, some posture monitor and alarm systems have been developed. U.S. Pat. No. 5,038,137 and U.S. Pat. No. 5,914,660 disclose a monitor and alarm system or apparatus using carry-on sensors. However, an individual will feel uncomfortable to carry the carry-on sensors all the time.

U.S. Pat. No. 5,184,112 discloses an apparatus for monitoring the position of a patient in bed, and U.S. Pat. No. 5,884,488 discloses an early warning bed egress alarm system. Both patents use pressure sensors to detect the position of a patient. The disclosed apparatus and system can detect only the patient's position, but cannot tell whether the patient has remained in a fixed posture for a long time.

U.S. Pat. No. 6,468,234 discloses a method and apparatus for measuring sleep quality that utilizes sensors incorporated in a sheet laid on top of a conventional mattress. The sensors can collect information such as the subject's position, body temperature, movement, mattress pressure, breathing and heart rate, as well as episodes of snoring and teeth grinding (bruxism). Nevertheless, the apparatus cannot identify body posture.

U.S. Pat. No. 6,791,460 discloses a patient position detection system having at least three different modes of operation. However, the system cannot detect the posture of a patient.

"Monitoring patient respiration and posture using human symbiosis system" by Nishida et al, Intelligent Robots and Systems, Proceedings of the 1997 IEEE/RSJ International Conference on IROS '97, Vol. 2, pp. 632-639, 1997, teaches a system having a microphone, CCD (Charge Coupled Device) and 221 force sensing resistors. The disclosed system applies a threshold level to sensor values generated by force sensing resistors, and determines body posture based on the distribution of the sensor values. However, the system may easily misjudge the posture and require more sensors.

"Body parts positions and posture estimation system based on pressure distribution image" by Harada et al, IEEE Proc. of International Conference on Robotics and Automation, Vol. 2, pp. 968-975, 1999, teaches a system that detects body position and posture using pressure distribution image analysis method. This system requires more sensors and consumes more system resources, and doesn't have a user adaptation mechanism.

"Infant Behavior Recognition System Based on Pressure Distribution Image" by Harada et al, Proceeding of the 2000 IEEE International Conference on Robotics and Automation, San Francisco, pp. 4082-4088, 2000, teaches a system for recognizing an infant's behavior. The system requires more sensors and is only applied to infants.

"Estimation of Bed-Ridden Human's Gross and Slight Movement Based on Pressure Sensors Distribution Bed" by Harada, ICRA 2002: 3795-3800, discloses a system that can identify the object in bed, which is an object or a human being, measure breathing rate and recognize lying postures, sit-up position or movement of arms. The system requires more sensors and consumes a lot of system resources, and furthermore, doesn't have a user adaptation mechanism.

In conclusion, present systems or apparatuses suffering from some deficiencies cannot meet the future requirement of elderly healthcare. Therefore, a new system without the above-mentioned deficiencies shall be developed.

SUMMARY OF THE INVENTION

The present invention proposes a method for contour fitting and posture identification, which initially receives sensor data, composed of a plurality of sensor signals correlated with a user posture, in a nearly real-time manner, and then a contour or posture analysis is performed on the sensor data and at least one candidate posture is determined from a set of at least one posture model based on the sensor data.

The present invention proposes a method for contour model adaptation, which initially receives sensor data, which is measured from a user who is the adaptation target, and such data corresponds to the posture of the user. Then at least one characteristic value is obtained by analyzing the received sensor data. Thereafter, a parameter of the posture model corresponding to the posture is calculated based on the at least one characteristic value. Finally, the posture model is modified using the parameter.

The present invention proposes a system, according to one embodiment, for contour fitting and posture identification, which comprises a sensing device configured for generating sensor data composed of a plurality of sensor signals, each of which is generated by a corresponding sensor; a control device configured for receiving the sensor data through a network; and a computing device coupled to the control device, configured to process the sensor data. The computing device comprises a receiving module configured for receiving the sensor signals; and a posture identification module configured for determining a user posture based on the sensor data.

The present invention proposes a system, according to another embodiment, for contour fitting and posture identification, which comprises a sensing device configured for generating sensor data composed of a plurality of sensor signals, each of which is generated by a corresponding sensor; and a control device configured for receiving the sensor data through a network. The control device comprises a receiving module configured for receiving the sensor signals; and a posture identification module configured for determining a user posture based on the sensor data.

BRIEF DESCRIPTION OF THE DRAWINGS

The invention will be described according to the appended drawings in which.

DETAILED DESCRIPTION OF THE INVENTION

Figure 1:
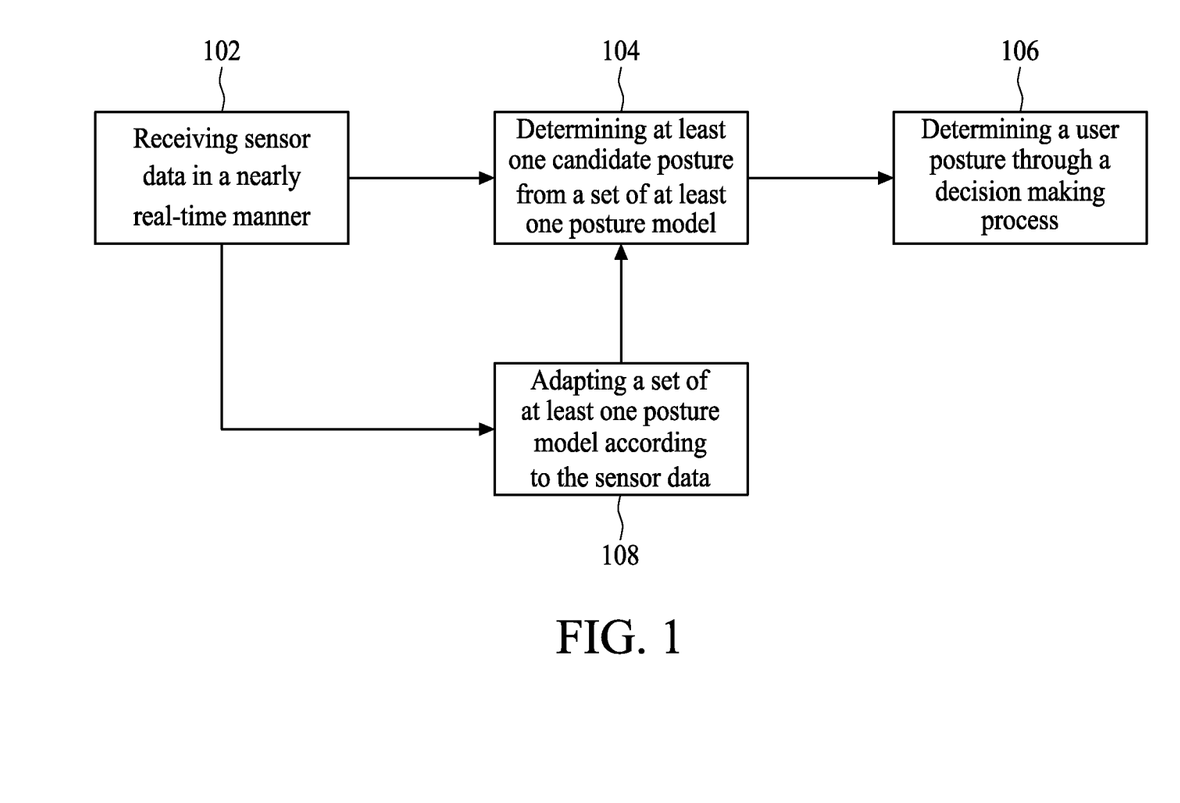
FIG. 1 is a flow diagram illustrating a method for contour fitting and posture identification according to one embodiment of the present invention.

FIG. 1 is a flow diagram illustrating a method for contour fitting and posture identification according to one embodiment of the present invention. The method proposed by the present invention initially receives sensor data in a nearly real-time manner (102). The sensor data comprises a plurality of sensor signals correlated with a user posture. Each sensor signal is generated by a corresponding sensor thereof and is acquired via a network. The acquisition frequency of each sensor signal is adjusted automatically based on an evaluation result of the sensor signal so that the sensor signals are received in a nearly real-time manner. Thereafter, a contour or posture analysis is performed on the sensor data. At least one candidate posture is determined from a set of at least one posture model based on the sensor data (104). Finally, a user posture is determined from the at least one candidate posture through a decision making process (106), which can lower the risk of erroneous judgment. Moreover, the method of the present invention can also adapt each posture model in the set of at least one posture model to each different user's personal habitual behavior according to the sensor data (108) so as to increase the posture detection reliability. In the present embodiment, the set of at least one posture model is established by extracting features representing supine, left side lying and right side lying postures.

Figure 2:
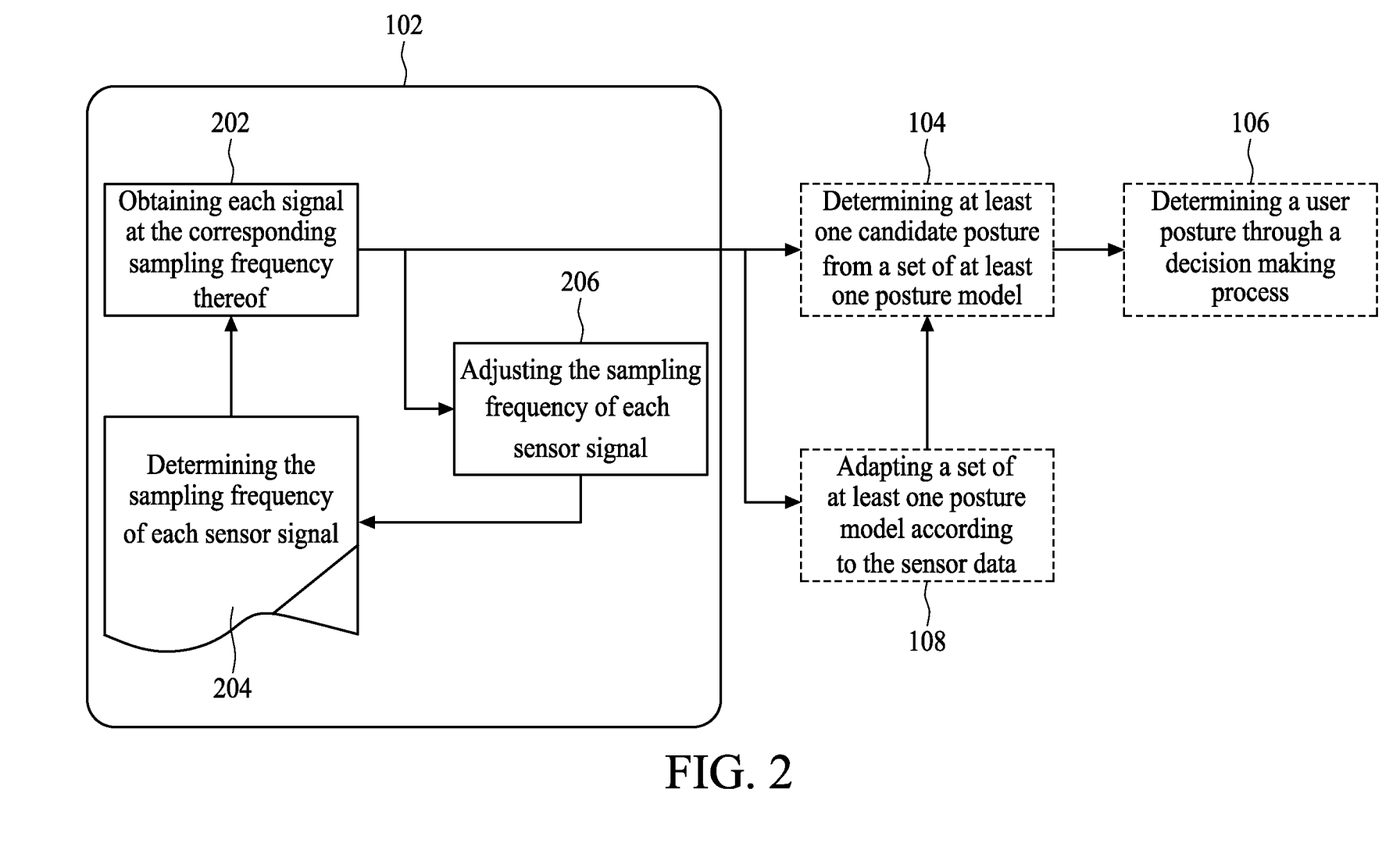
FIG. 2 is a flow diagram illustrating a method for receiving sensor signals in nearly real-time manner according to one embodiment of the present invention.

FIG. 2 is a flow diagram illustrating a method for receiving sensor signals in a nearly real-time manner according to one embodiment of the present invention. The method initially determines the sampling frequency of each sensor signal (204). Thereafter, each signal is obtained at the corresponding sampling frequency thereof (202). The sampling frequency is dynamically adjusted, and thus the method further comprises the step of adjusting the sampling frequency of each sensor signal based on an evaluation result of the sensor signal (206). Due to the adjustment mechanism of the sampling frequency, the sensor signals can be received in nearly real time. The evaluation result comprises a result of comparison between the sensor signal and a threshold, a value variation of the sensor signal and a rate of the value variation of the sensor signal.

Figure 3:
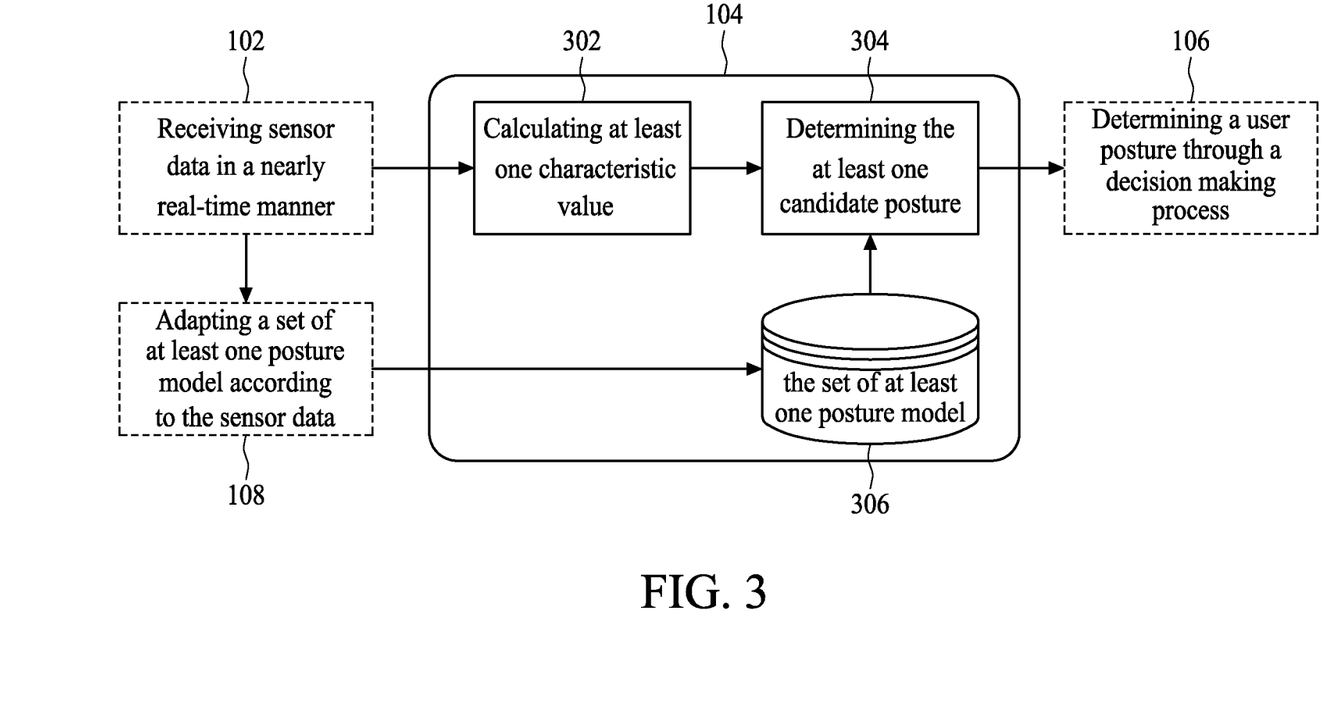
FIG. 3 is a flow diagram illustrating a method for determining at least one candidate posture according to one embodiment of the present invention.

FIG. 3 is a flow diagram illustrating a method for determining at least one candidate posture according to one embodiment of the present invention. The method for determining a candidate posture first calculates at least one characteristic value based on the sensor data (302). The at least one characteristic value comprises at least one of a center of gravity location, an average estimate of the sensor signals, a standard deviation of the sensor signals, a kurtosis estimate of the probability distribution from the sensor signals and a skewness estimate of the probability distribution from the sensor signals, and the candidate posture determination can be based on one or more values described above. Next, the at least one candidate posture is determined by comparing the at least one characteristic value with the set of at least one posture model (304), which is stored in a database (306). In the method, the probability of each type of posture will also be evaluated.

In the present embodiment, the sensor signals are normalized and regarded as a probability distribution. The kurtosis estimate of the probability distribution and the skewness estimate of the probability distribution are calculated by equations (a) and (b) separately below.

$$\text{Kurtosis} = \left\{ \frac{n(n+1)}{(n-1)(n-2)(n-3)} \sum \left( \frac{x_i - \bar{x}}{s} \right)^4 \right\} - \frac{3(n-1)^2}{(n-2)(n-3)} \quad (a)$$

$$\text{Skewness} = \frac{n}{(n-1)(n-2)} \sum \left( \frac{x_i - \bar{x}}{s} \right)^3 \quad (b)$$

Where n is the number of simulated samples of the probability distribution, s is a sample standard deviation, $x_i$ represents the simulated sample, and $\bar{x}$ is the mean of the probability distribution.

Each posture model used in the step of determining the at least one candidate posture comprises a posture template or a posture probability model. In the present embodiment, each of the posture templates is a representation of one user posture in the parameter space. The parameter space, a two dimensional space in the present embodiment, is constructed by using a kurtosis estimate and a skewness estimate. Each posture template can be an expected value vector, which is calculated based on the sensor data of the same corresponding posture, represented by $\mu_\omega[E(k),E(s)]'$, where $\omega$ is a posture, E(k) and E(s) are expected values of kurtosis and skewness correspondingly. The postures, $\omega$, comprise supine body posture, left side lying body posture and right side lying body posture. The determination of a candidate posture is based on the closeness between sensor data and each posture model, and the closeness is measured by a match value. The match value is a distance or a similarity measure. If a posture template is used for the determination of a candidate posture, the match value can be a distance such as a Euclidean distance or Mahalanobis distance.

In one embodiment of the present invention, the posture probability model is the normal distribution model. For example, when a feature vector X=[Kurtosis, Skewness]' is given, the probability of the supine body posture can be calculated using the following equation (c):

$$P(X \mid \omega = \text{supine}) = \qquad (c)$$

$$\frac{1}{\sqrt{2\pi\sigma^2_{supine-kurt}}} \exp\left(-\frac{1}{2}\frac{(\text{kurtosis} - \mu_{supine-kurt})^2}{\sigma^2_{supine-kurt}}\right) \times$$

$$\frac{1}{\sqrt{2\pi\sigma^2_{supine-skew}}} \exp\left(-\frac{1}{2}\frac{(\text{skewness} - \mu_{supine-skew})^2}{\sigma^2_{supine-skew}}\right)$$

where $\mu_{supine-kurt}$, $\sigma_{supine-kurt}$, $\mu_{supine-skew}$ and $\sigma_{supine-skew}$ are posture model parameters of the supine body posture. The posture model parameters, which are predetermined, comprise an average kurtosis of each posture, an average skewness of each posture, a standard deviation of the kurtosis estimates of each posture and a standard deviation of the skewness estimates of each posture. The determination of a candidate posture is based on the match value, which is a distance or a similarity measure. If the determination is based on the match value of distance, the candidate posture, which has the shortest Mahalanobis distance, will be selected; if the determination is based on the match value of similarity, the candidate posture with the largest probability will be selected.

Figure 4:
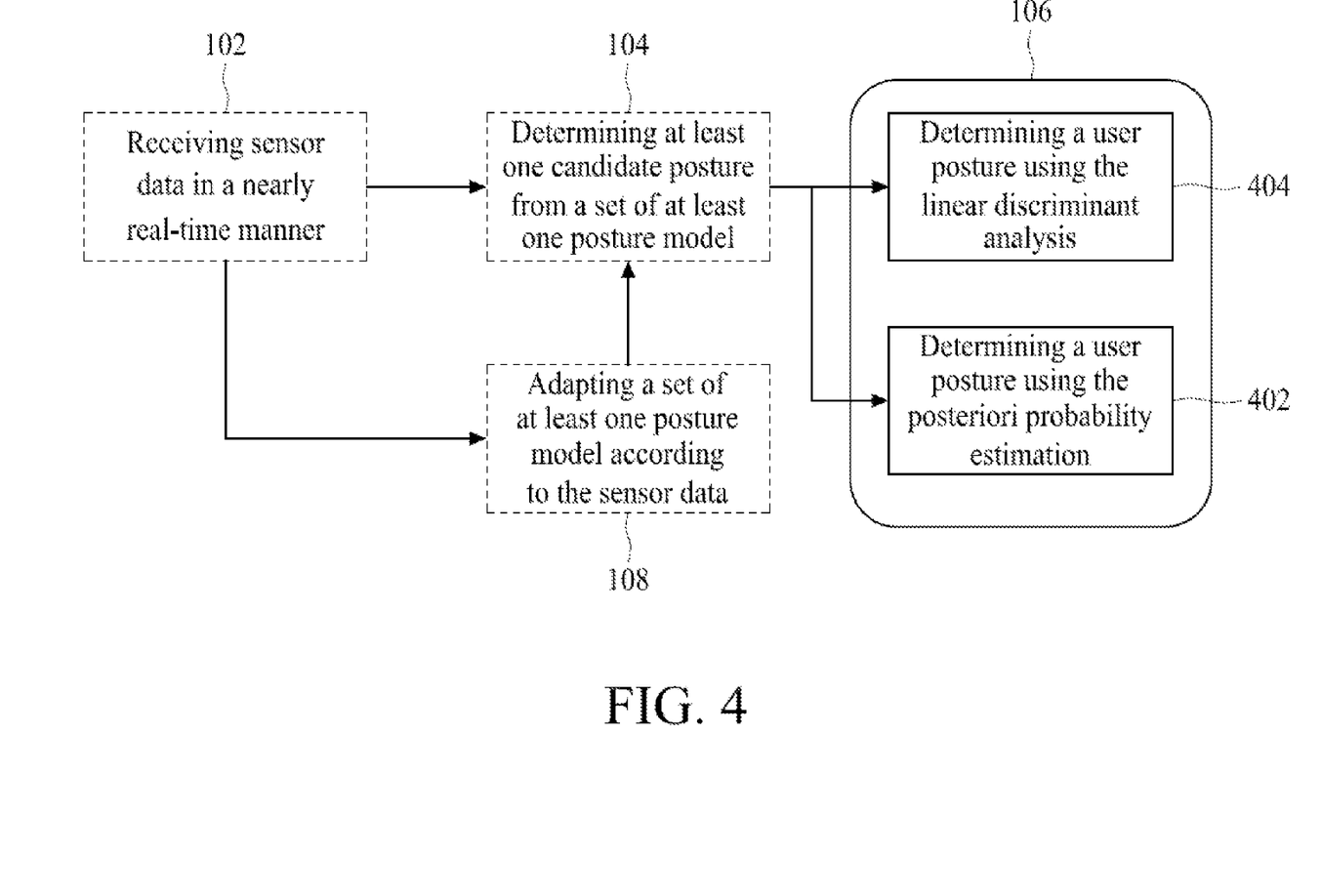
FIG. 4 is a flow diagram illustrating a method for determining a user posture according to one embodiment of the present invention.

FIG. 4 is a flow diagram illustrating a method for determining a user posture according to one embodiment of the present invention. In order to lower the error rate of determining a user posture, the match values are analyzed through a decision-making process, which is based on posteriori probability estimation and linear discriminant analysis. The most probable user posture can be determined on the analysis of the match values using the posteriori probability estimation (402) and/or can be determined using the linear discriminant analysis (404).

In one embodiment, the determination of a user posture is based on Bayesian decision strategy. The most probable user posture is determined using posteriori probability estimation equation, such as equation (d) below:

$$\hat{\omega} = \underset{\omega}{\arg\max}\, P(\omega \mid X) = \underset{\omega}{\arg\max}\, \frac{P(X \mid \omega)P(\omega)}{P(X)} = \underset{\omega}{\arg\max}\, P(X \mid \omega)P(\omega) \qquad (d)$$

where $\hat{\omega}$ is the most probable user posture; $\omega$ are all candidate postures; $X=[\text{Kurtosis},\text{Skewness}]'$ is a feature vector; and $P(X|\omega)$ is a class-conditional probability.

In another embodiment, the Bayesian decision strategy used to determine the most probable user posture is performed using linear discriminant analysis, which analyzes any two posture models using equation (e) below.

$$E_{1,2}: P(X|\omega_1)P(\omega_1) = P(X|\omega_2)P(\omega_2) \qquad (e)$$

where $\omega_1$ and $\omega_2$ represents any two candidate postures.

For example, if a supine body posture and a left side lying posture are analyzed, the equation (e) becomes the following:

$$E_{supine,leftsidelying}: P(X|\omega=\text{supine})P(\omega=\text{supine}) = P(X|\omega=\text{left side lying})P(\omega=\text{left side lying}) \qquad (f)$$

Under the uniform variance assumption, the equation (f) can be simplified to equation (g) below.

$$E_{supine,leftlying}: \left(\begin{bmatrix} \sigma^2_{kurt,kurt} & \sigma^2_{kurt,skew} \\ \sigma^2_{kurt,skew} & \sigma^2_{skew,skew} \end{bmatrix}^{-1} (\mu_{supine} - \mu_{leftlying})\right)' X = \qquad (g)$$

-continued $$\frac{1}{2}(\mu_{supine} + \mu_{leftlying}) \begin{bmatrix} \sigma^2_{kurt,kurt} & \sigma^2_{kurt,skew} \\ \sigma^2_{kurt,skew} & \sigma^2_{skew,skew} \end{bmatrix}^{-1} (\mu_{supine} - \mu_{leftlying})$$

Figure 5:
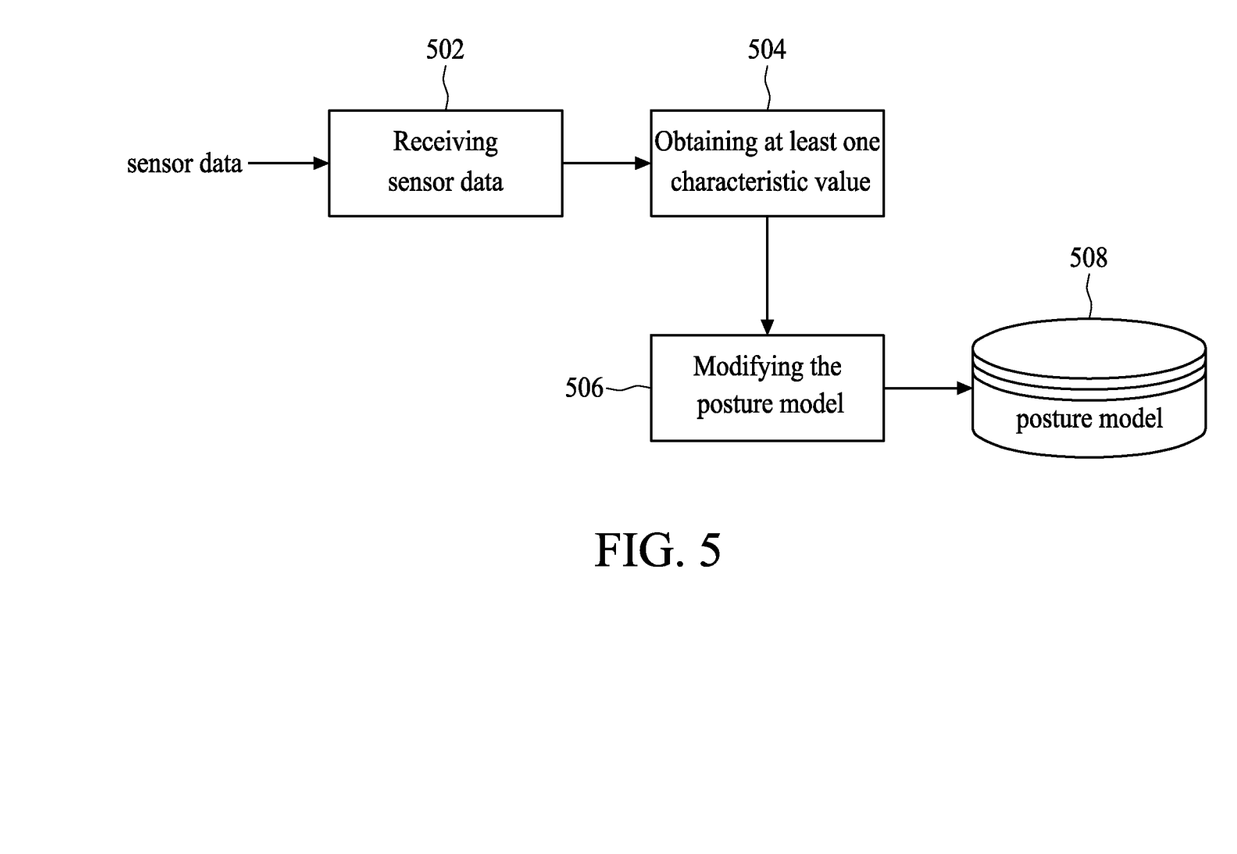
FIG. 5 is a flow diagram illustrating a method for contour model adaptation according to one embodiment of the present invention.

FIG. 5 is a flow diagram illustrating a method for contour model adaptation according to one embodiment of the present invention. Because everybody has different body shape and size, and different habitual behavior, the posture models of different people may be different. The present invention provides a method for contour model adaptation, which is used to modify posture models according to the body shape and size of every individual, to increase the accuracy of user posture determination. The contour model adaptation method initially receives sensor data, which are measured from a user who is the adaptation target and is corresponding to the posture of the user (502). The method uses sensor data of one posture to adapt the posture model of that posture. Then, at least one characteristic value is obtained by analyzing the received sensor data (504). In the present embodiment, the at least one characteristic value comprises at least one of a center of gravity location, an average estimate of the sensor signals, a standard deviation of the sensor signals, a kurtosis estimate of the probability distribution from the sensor signals and a skewness estimate of the probability distribution from the sensor signals. Thereafter, a set of parameters of the posture model 508 corresponding to the posture is calculated based on the at least one characteristic value. Finally, the posture model 508 is modified using the set of parameters (506).

Figure 6:
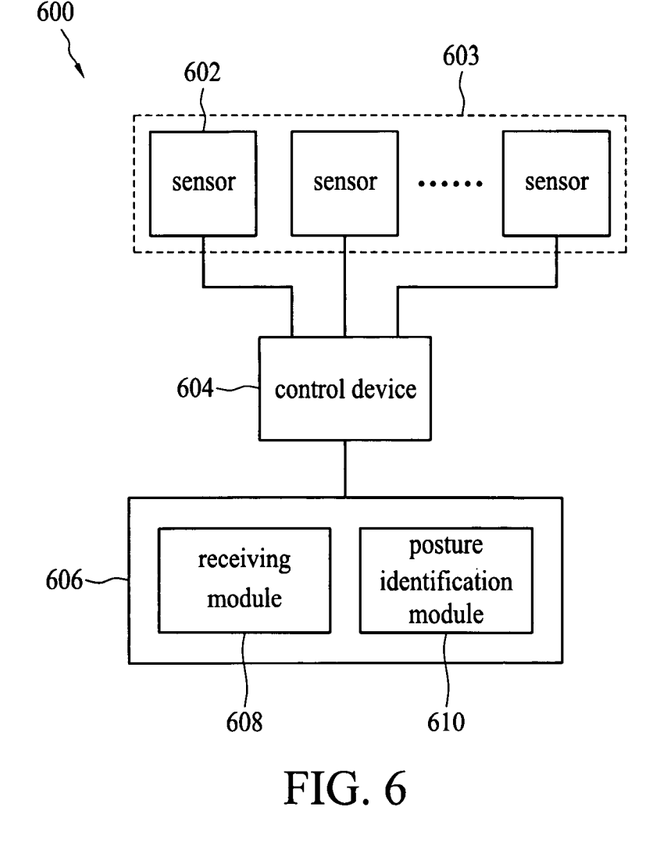
FIG. 6 shows a system for contour fitting and posture identification according to one embodiment of the present invention.

FIG. 6 shows a system for contour fitting and posture identification according to one embodiment of the present invention. The system (600) for contour fitting and posture identification comprises a sensing device (603) configured for generating sensor data composed of a plurality of sensor signals, wherein each sensor signal is generated by a corresponding sensor (602); a control device (604) configured for receiving the sensor data through a network; and a computing device (606) coupled to the control device (604), configured to process the sensor data. The computing device (606) comprises a receiving module (608) configured for receiving the sensor signals; and a posture identification module (610) configured for determining a user posture based on the sensor data. In one embodiment, the network comprises a wired network or a wireless network, and the network topology of the network comprises a mesh topology, a star topology, a bus topology, a ring topology or a tree topology.

Figure 7:
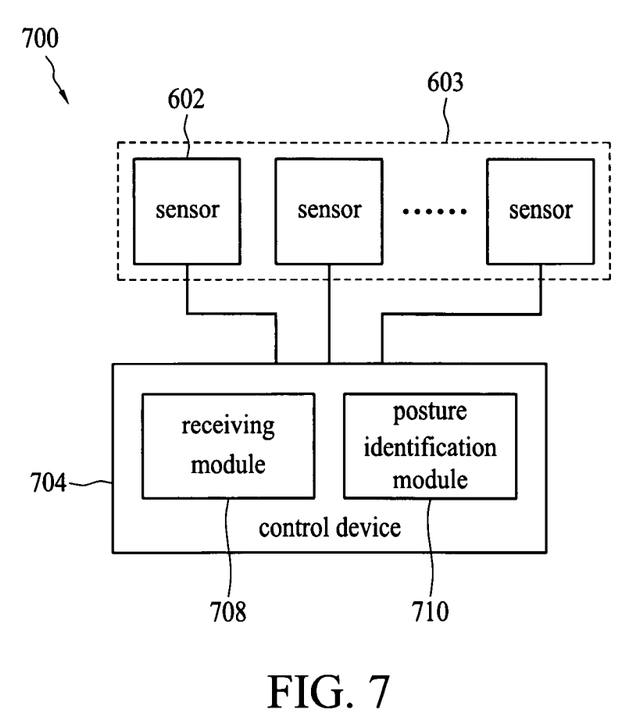
FIG. 7 shows a system for contour fitting and posture identification according to another embodiment of the present invention.

FIG. 7 shows a system for contour fitting and posture identification according to another embodiment of the present invention. The system (700) for contour fitting and posture identification comprises a sensing device (603) configured for generating sensor data composed of a plurality of sensor signals, wherein each sensor signal is generated by a corresponding sensor (602); and a control device (704) configured for receiving the sensor data through a network. The control device (704) comprises a receiving module (708) configured for receiving the sensor signals; and a posture identification module (710) configured for determining a user posture based on the sensor data.

Figure 8:
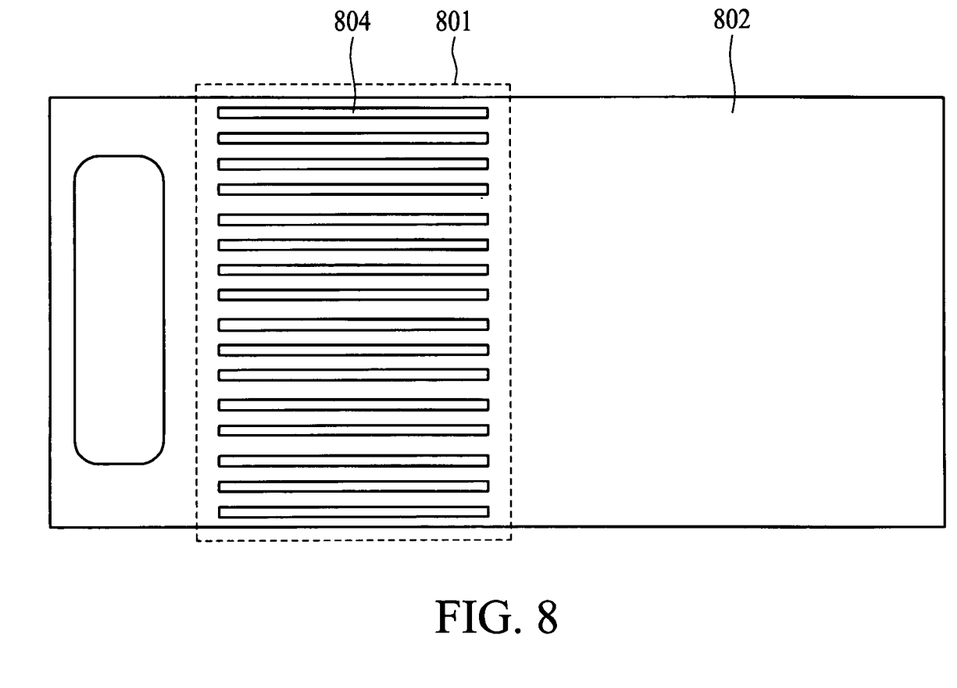
FIG. 8 shows a sensing device according to one embodiment of the present invention.

FIG. 8 shows a sensing device according to one embodiment of the present invention. The sensing device (801) comprises a plurality of sensors (804) used to generate sensor signals. The sensing device (801) can be disposed on the upper portion of a bed (802). In the present embodiment, the sensor (804) comprises a pressure sensor. The sensor signal generated by the sensor (804) is a current signal, a voltage signal or a resistance signal.

In summary, compared to the described prior arts, the present invention provides a method and a system using the same, which can identify a user posture without any carry-on sensor; doesn't need a lot of sensors; can receive signals in nearly real time without requirement of much system resources; have a user adaptation mechanism to increase the accuracy of posture identification; and increase the reliability of the determination of a user posture by applying decision-making strategies.

The above-described embodiments of the present invention are intended to be illustrative only. Numerous alternative embodiments may be devised by person skilled in the art without departing from the scope of the following claims.

What is claimed is:

1. A method for posture identification, comprising the steps of:
   receiving, using a control device, sensor data formed of a plurality of sensor signals correlated with a user posture of a user from a plurality of sensors;
   determining, using the control device, at least one candidate posture from a set of at least one posture model based on the sensor data; and
   determining, using the control device, the user posture from the at least one candidate posture through a decision-making process,
   wherein the receiving step comprises the steps of:
      determining at least one sampling frequency of the sensor signals;
      obtaining the sensor signals according to the at least one sampling frequency; and
      adjusting the at least one sampling frequency of the sensor signals based on an evaluation result of the sensor signals; and
   wherein the step of determining, using the control device, the at least one candidate posture comprises the steps of:
      calculating characteristic values comprising a kurtosis estimate and a skewness estimate of a probability distribution from the plurality of sensor signals; and
      determining the at least one candidate posture by applying the characteristic values to each posture model in the set of at least one posture model.

2. The method of claim 1, further comprising a step of modifying one posture model in the set of at least one posture model based on sensor data of a corresponding predetermined posture of the user to adapt the posture model to the user.

3. The method of claim 1, wherein the set of at least one posture model comprises a supine body posture, a left side lying body posture, and a right side lying body posture.

4. The method of claim 1, wherein the plurality of sensors comprise pressure sensors.

5. The method of claim 1, wherein each posture model in the set of at least one posture model comprises a posture template or a posture probability model.

6. The method of claim 5, wherein the step of determining, using the control device, the at least one candidate posture further comprises a step of:
   determining the at least one candidate posture based on the analysis of a corresponding match value, wherein the corresponding match value is a distance or a similarity measure.

7. The method of claim 1, wherein the decision-making process is based on maximum posteriori probability estimation and linear discriminant analysis.

8. The method of claim 1, wherein the kurtosis estimate and the skewness estimate are calculated by following equations:

$$\text{Kurtosis} = \left\{ \frac{n(n+1)}{(n-1)(n-2)(n-3)} \Sigma \left( \frac{x_i - \bar{x}}{s} \right)^4 \right\} - \frac{3(n-1)^2}{(n-2)(n-3)}$$

$$\text{Skewness} = \frac{n}{(n-1)(n-2)} \Sigma \left( \frac{x_i - \bar{x}}{s} \right)^3$$

wherein Kurtosis is the kurtosis estimate, Skewness is the skewness estimate, n is a number of samples of the probability distribution, s is a sample standard deviation of the probability distribution, $x_i$ is a sample of the probability distribution, and $\bar{x}$ is a mean of the probability distribution.

9. The method of claim 1, wherein a posture model in the set of at least one posture model is represented by a following equation:

$$P(X \mid \omega = \text{pos}) = \frac{1}{\sqrt{2\pi\sigma^2_{pos-kurt}}} \exp\left(-\frac{1}{2} \frac{(\text{kurtosis} - \mu_{pos-kurt})^2}{\sigma^2_{pos-kurt}}\right) \times$$

$$\frac{1}{\sqrt{2\pi\sigma^2_{pos-skew}}} \exp\left(-\frac{1}{2} \frac{(\text{skewness} - \mu_{pos-skew})^2}{\sigma^2_{pos-skew}}\right)$$

wherein pos is a first posture that the posture model corresponds to, kurtosis is the kurtosis estimate, skewness is the skewness estimate, $\mu_{pos-kurt}$, $\sigma_{pos-kurt}$, $\mu_{pos-skew}$ and $\sigma_{pos-skew}$ are posture model parameters and are an average kurtosis estimate of the first posture, a standard deviation of kurtosis estimates of the first posture, an average skewness estimate of the first posture, and a standard deviation of skewness estimates of the first posture, respectively.

10. The method of claim 1, wherein each posture model in the set of at least one posture model is a posture probability model.

11. The method of claim 10, wherein each posture model in the set of at least one posture model comprises posture model parameters, and the posture model parameters comprise an average kurtosis estimate of a corresponding posture of the posture model, a standard deviation of kurtosis estimates of the corresponding posture, an average skewness estimate of the corresponding posture, and a standard deviation of skewness estimates of the corresponding posture.

12. A method for posture model adaptation, comprising the steps of:
   receiving, using a control device, sensor data including a plurality of sensor signals corresponding to a predetermined posture from a plurality of sensors;
   obtaining, using the control device, characteristic values comprising a kurtosis estimate and a skewness estimate of a probability distribution from the plurality of sensor signals;
   calculating, using the control device, posture model parameters of a posture model corresponding to the predetermined posture based on the characteristic values; and
   modifying, using the control device, the posture model by using the posture model parameters,
   wherein the receiving step comprises steps of:
      determining at least one sampling frequency of the sensor signals;
      obtaining the sensor signals according to the at least one sampling frequency; and adjusting the at least one sampling frequency of the sensor signals based on an evaluation result of the sensor signals.

13. The method of claim 12, wherein the posture model is a posture probability model.

14. The method of claim 13, wherein the posture model parameters comprise an average kurtosis estimate of the predetermined posture, a standard deviation of kurtosis estimates of the predetermined posture, an average skewness estimate of the predetermined posture, and a standard deviation of skewness estimates of the predetermined posture.

15. The method of claim 12, wherein the kurtosis estimate and the skewness estimate are calculated by following equations:

$$\text{Kurtosis} = \left\{ \frac{n(n+1)}{(n-1)(n-2)(n-3)} \Sigma \left( \frac{x_i - \bar{x}}{s} \right)^4 \right\} - \frac{3(n-1)^2}{(n-2)(n-3)}$$

$$\text{Skewness} = \frac{n}{(n-1)(n-2)} \Sigma \left( \frac{x_i - \bar{x}}{s} \right)^3$$

wherein Kurtosis is the kurtosis estimate, Skewness is the skewness estimate, n is a number of samples of the probability distribution, s is a sample standard deviation of the probability distribution, $x_i$ is a sample of the probability distribution, and $\bar{x}$ is a mean of the probability distribution.

16. A system for posture identification, comprising:
a sensing device configured for generating sensor data having a plurality of sensor signals correlated with a user posture, wherein each sensor signal is generated by a corresponding sensor; and
a control device configured for receiving the sensor data through a network and determining the user posture based on the sensor data, the control device comprising:
a receiving module configured to perform a receiving method to receive the sensor signals, wherein the receiving method comprises the steps of:
determining at least one sampling frequency of the sensor signals;
obtaining the sensor signals according to the at least one sampling frequency; and
adjusting the at least one sampling frequency of the sensor signals based on an evaluation result of the sensor signals; and
a posture identification module configured to perform a determining method to determine the user posture based on the sensor data, wherein the determining method comprises the steps of:
determining at least one candidate posture from a set of at least one posture model based on the sensor data; and
determining the user posture from the at least one candidate posture through a decision-making process,
wherein the step of determining the at least one candidate posture comprises the steps of:
calculating characteristic values comprising a kurtosis estimate and a skewness estimate of a probability distribution from the plurality of sensor signals; and
determining the at least one candidate posture by applying the characteristic values to each posture model in the set of at least one posture model.

17. The system of claim 16, wherein the plurality of sensors comprise pressure sensors.

18. The system of claim 16, wherein the network comprises a wired network or a wireless network.

19. The system of claim 16, wherein a network topology of the network comprises a mesh topology, a star topology, a bus topology, a ring topology or a tree topology.

20. The system of claim 16, wherein each sensor signal is a current signal, a voltage signal or a resistance signal.

21. A system for posture identification, comprising:
a sensing device configured for generating sensor data having a plurality of sensor signals correlated with a user posture, wherein each sensor signal is generated by a corresponding sensor;
a control device configured for receiving the sensor data through a network; and
a computing device coupled to the control device, the computing device configured to process the sensor data and comprising:
a receiving hardware module configured to perform a receiving method to receive the sensor signals, wherein the receiving method comprises the steps of:
determining at least one sampling frequency of the sensor signals;
obtaining the sensor signals according to the at least one sampling frequency; and
adjusting the at least one sampling frequency of the sensor signals based on an evaluation result of the sensor signals; and
a posture identification module configured to perform a determining method to determine the user posture based on the sensor data, wherein the determining method comprises the steps of:
determining at least one candidate posture from a set of at least one posture model based on the sensor data; and
determining the user posture from the at least one candidate posture through a decision-making process,
wherein the step of determining the at least one candidate posture comprises the steps of:
calculating characteristic values comprising a kurtosis estimate and a skewness estimate of a probability distribution from the plurality of sensor signals; and
determining the at least one candidate posture by applying the characteristic values to each posture model in the set of at least one posture model.

* * * * *